(12) United States Patent
Orth et al.

(10) Patent No.: US 6,589,225 B2
(45) Date of Patent: Jul. 8, 2003

(54) METHODS, SYSTEMS, AND KITS FOR IMPLANTING ARTICLES

(75) Inventors: Michael J. Orth, Morgan Hill, CA (US); Mark C. Yang, Mountain View, CA (US)

(73) Assignee: Innerdyne, Inc., Norwalk, CT (US)

( * ) Notice: Subject to any disclaimer, the term of this patent is extended or adjusted under 35 U.S.C. 154(b) by 0 days.

(21) Appl. No.: 09/823,934

(22) Filed: Mar. 30, 2001

(65) Prior Publication Data

US 2002/0002360 A1 Jan. 3, 2002

Related U.S. Application Data

(63) Continuation of application No. 09/112,102, filed on Jul. 8, 1998, now Pat. No. 6,245,052.

(51) Int. Cl.⁷ .............................................. A61M 31/00
(52) U.S. Cl. .................... 604/506; 604/890.1; 604/104; 604/164.1; 604/164.11; 604/264; 604/60; 606/185
(58) Field of Search ................................ 604/500, 502, 604/506, 57, 104, 107, 164.01, 171, 890.1, 891.1, 19, 48, 511, 59, 60, 93.01, 164.03, 164.09, 164.1, 164.11, 523, 264, 527, 524; 623/1.42, 1.1, 1.11, 1.46–1.48, 11.11, 14.13, 13.11–13.19, 23.7; 606/108, 191, 167, 185

(56) References Cited

U.S. PATENT DOCUMENTS

| | | | |
|---|---|---|---|
| 3,788,318 A | | 1/1974 | Kim et al. |
| 4,411,655 A | | 10/1983 | Schreck |
| 4,716,901 A | | 1/1988 | Jackson et al. |
| 4,753,636 A | | 6/1988 | Free |
| 4,899,729 A | | 2/1990 | Gill et al. |
| 4,941,874 A | * | 7/1990 | Sandow et al. .............. 604/60 |
| 5,021,241 A | * | 6/1991 | Yamahira et al. ........... 424/426 |
| 5,183,464 A | | 2/1993 | Dubrul et al. |
| 5,201,756 A | | 4/1993 | Horzewski et al. |
| 5,279,554 A | | 1/1994 | Turley |
| 5,304,119 A | | 4/1994 | Balaban et al. |
| 5,403,278 A | * | 4/1995 | Ernst et al. .................. 604/60 |
| 5,431,676 A | | 7/1995 | Dubrul et al. |
| 5,453,094 A | | 9/1995 | Metcalf et al. |
| 5,454,790 A | | 10/1995 | Dubrul |
| 5,484,403 A | | 1/1996 | Yoakum et al. |
| 5,487,739 A | | 1/1996 | Aebischer et al. |
| 5,674,240 A | | 10/1997 | Bonutti et al. |
| 5,713,867 A | | 2/1998 | Morris |
| 5,800,390 A | * | 9/1998 | Hayakawa et al. ....... 604/93.01 |
| 5,827,319 A | | 10/1998 | Carlson et al. |
| 5,961,499 A | | 10/1999 | Bonutti et al. |
| 6,095,967 A | * | 8/2000 | Black et al. .................. 600/7 |
| 6,325,789 B1 | * | 12/2001 | Janzen et al. ............... 604/506 |

FOREIGN PATENT DOCUMENTS

GB 2199247 7/1988

* cited by examiner

*Primary Examiner*—Brian L. Casler
*Assistant Examiner*—Cris L. Rodriguez (57) ABSTRACT

Methods, systems, and kits for subcutaneously implanting articles, such as drug inserts and reservoirs. The methods rely on percutaneously forming a tissue tract and radially dilating the tract to a diameter which permits introduction of the article. By fully expanding the lumenal diameter of the tissue tract prior to introduction of the article, damage to the article resulting from passage through a partially expanded tissue tract can be avoided. In the exemplary embodiment, a radially expandable sleeve is first percutaneously introduced to the subcutaneous target site. An assembly of a cannula and dilator is then passed through the sleeve, effecting radial expansion. The dilator is removed and the article is then introduced through a lumen of the cannula.

16 Claims, 7 Drawing Sheets

METHODS, SYSTEMS, AND KITS FOR IMPLANTING ARTICLES

CROSS-REFERENCES TO RELATED APPLICATIONS

The present application is a continuation of, and claims the benefit of priority from U.S. application No. 09/112,102 filed Jul. 8, 1998 now U.S. Pat. No. 6,245,052, the full disclosure of which is incorporated herein by reference.

BACKGROUND OF THE INVENTION

1. Field of the Invention

The present invention relates generally to medical methods, apparatus, and kits. More particularly, the present invention relates to methods, systems, and kits for percutaneously delivering implantable articles, such as subcutaneous drug inserts, to solid tissue locations.

Implantable articles are useful for a wide variety of medical purposes. Of particular interest to the present invention, drug inserts and controlled release reservoirs may be subcutaneously implanted in order to release a drug or other biologically active substance over time. Usually, the insert or reservoir will be implanted intramuscularly or intraperitoneally by first forming an incision which permits the article to be implanted at the target site. Often, a large bore needle or cannula is used to inject the insert or reservoir to the target location. Such devices, however, often result in coring of the tissue, and subsequent injection of the drug insert pushes against such cored tissue, rendering placement difficult. While such problems have been at least partly overcome by the use of trocar/cannula assemblies where the trocar cuts through tissue, the use of relatively large diameter trocars is traumatic to the patient and can leave scarring.

An improvement over the use of large diameter needles and trocars is proposed in U.S. Pat. No. 5,304,119. The '119 patent teaches use of a tapered cannula having a pair of opposed tines overs its distal end. The tines meet together in a "duck bill" fashion and may be advanced through solid tissue with reduced trauma to the patient. After initial placement of the cannula, a drug insert may be advanced axially through the device, forcing the opposed tines to open and permitting placement of the insert at the desired target location. While workable and an improvement over prior delivery systems, reliance on passage of the drug insert to open the opposed tines can be problematic. In particular, the mechanical action can physically damage the drug insert prior to its delivery to the tissue target site.

For these reasons, it would be desirable to provide improved methods, systems, and kits for delivering implantable articles, such as drug inserts and controlled release reservoirs, to solid tissue locations. In particular, it would be desirable to provide for percutaneous delivery of such articles in a manner which is both minimally traumatic to the patient and minimally damaging to the article. At least some these objectives will be met by the invention described hereinafter.

2. Description of the Background Art

A device and method for injecting implants are described in U.S. Pat. No. 5,304,119, discussed in more detail above. Radially expanding dilators of a type suitable for use in the methods of the present invention are described in U.S. Pat. Nos. 5,183,464 and 5,431,676, and are commercially available under the tradename STEP from InnerDyne, Inc., Sunnyvale, Calif., assignee of the present application. Other pertinent patents include U.S. Pat. Nos. 5,674,240; 5,484,403; 5,403,278; 5,201,756; 4,899,729; 4,716,901; and 3,788,318.

BRIEF SUMMARY OF THE INVENTION

According to the present invention, improved methods, systems, and kits are provided for implanting articles in solid tissue. The articles will usually be intended for drug delivery, typically being drug delivery inserts or reservoirs intended for controlled release of the drugs, but could also be intended for other purposes such as the delivery of brachytherapy seeds, pacemakers and other stimulatory devices and leads, pumps, transducers and other diagnostic and monitoring devices, sensors, and the like. The methods and systems of the present invention are characterized by the formation and radial expansion of a tissue tract from the surface of a patient's skin to a target site beneath the skin, typically within solid tissue (e.g., muscle), beneath the peritoneum, (i.e., the retroperitoneum), or the like. The tissue tract is radially expanded, preferably, to a substantially constant lumen diameter over its entire length, with the expansion occurring prior to introduction of the drug insert or other article. Radial expansion of the tissue tract is generally less traumatic to the patient than use of a large bore coring needle or large diameter trocar, and full expansion of the tissue tract prior to introduction of the article avoids the risk of damage to the article which can occur with systems such as that described in U.S. Pat. No. 5,304,119, where the article itself mechanically opens a path as it is advanced.

In a first aspect, a method according to the present invention comprises percutaneously inserting a radially expandable sleeve so that a distal end of the sleeve lies adjacent to a target site in solid tissue. An assembly comprising a cannula and a dilator is then introduced through the radially expandable sleeve, where the cannula and dilator have a diameter which is larger than an initial diameter of the sleeve so that the sleeve is radially expanded as the assembly is advanced distally through a lumen of the sleeve. Usually, the dilator will have a tapered or pointed distal end which facilitates advancement through the sleeve and which can extend beyond the distal end of the sleeve to penetrate the solid tissue and create a potential space for receiving the article to be implanted.

After the cannula/dilator assembly has been fully advanced within the sleeve, the dilator is removed from the cannula, leaving the cannula in place to maintain an open lumen having a diameter which is significantly greater than the initial lumen diameter of the sleeve. Usually, the lumenal diameter of the cannula will be in the range from 2 mm to 20 mm, preferably from 3 mm to 12 mm, most typically from 3 mm to 5 mm, while the initial lumen diameter of the sleeve will be less than 1 mm. After the dilator has been removed from the cannula, the article is advanced distally through the cannula lumen and beyond the distal end of the cannula so that it enters into the tissue where it is to be implanted. Conveniently, the article can be advanced using the same dilator which was originally used to advance the assembly of the cannula and dilator. Alternatively, a separate pusher rod or other element may be provided for insertion, advancement, and implantation of the article.

Usually, the percutaneous sleeve inserting step will comprise advancing an assembly of the sleeve and a needle directly into the tissue. The needle will usually be a small diameter, non-coring needle having a sharpened distal tip which extends distally of the sleeve to facilitate advancement of the assembly through the tissue. The needle may then be withdrawn proximally from the sleeve, leaving the sleeve in place to receive introduction of the assembly of the cannula and dilator in a subsequent step. In the exemplary embodiment, the expandable sleeve comprises a tubular braid formed from a mesh of non-elastic filaments which axially shorten as they are radially expanded.

The article will preferably be a drug delivery implant or controlled and sustained release reservoir. The article may be used for delivering a wide variety of drugs of the type which are suitable for subcutaneous intramuscular implantation, such as contraceptives, hormonal replacement, e.g. estrogen, progesterone, testostoronen, and the like.

In a second aspect, the method of the present invention comprises radially expanding a tissue tract to form a lumen having a substantially constant diameter over its entire length. The article to be implanted is then advanced distally through the lumen after the lumen has been substantially completely expanded. In this way, patient trauma is reduced while the risk of damage to the implanted article is minimized.

The present invention further comprises kits including a radially expandable sleeve, a cannula, and a dilator. The kit will further comprise instructions for use setting forth any of the methods described above. The kit usually will further comprise a container for holding the various kit components together, typically being a pouch, tray, box, tube, or the like. The kit components will usually be sterilized and maintained sterilely within the packaging, where sterilization can be effected by conventional means, such as radiation, exposure to ethyleneoxide, or the like. Optionally, the kit may further comprise the article to be implanted, typically being a pharmaceutical implant or reservoir.

The present invention still further comprises systems including both a radially expandable sleeve and a drug delivery article. The radially expandable sleeve will be expandable from a narrow diameter configuration which can be percutaneously introduced to the patient with lessened patient trauma and which will be radially expandable to a large diameter configuration in order to provide a non-collapsible lumen. The drug delivery article will have peripheral dimensions which permit it to be delivered through the non-collapsible lumen of the sleeve after radial expansion. The lumen of the sleeve will be capable of remaining fully open to its large diameter configuration even in the absence of the article so that the article may be passed through the lumen without the need for the article to help open the lumen. Usually, the radially expandable sleeve will be opened using an assembly of a cannula and a dilator as generally described above.

DESCRIPTION OF THE SPECIFIC EMBODIMENTS

Figure 1:
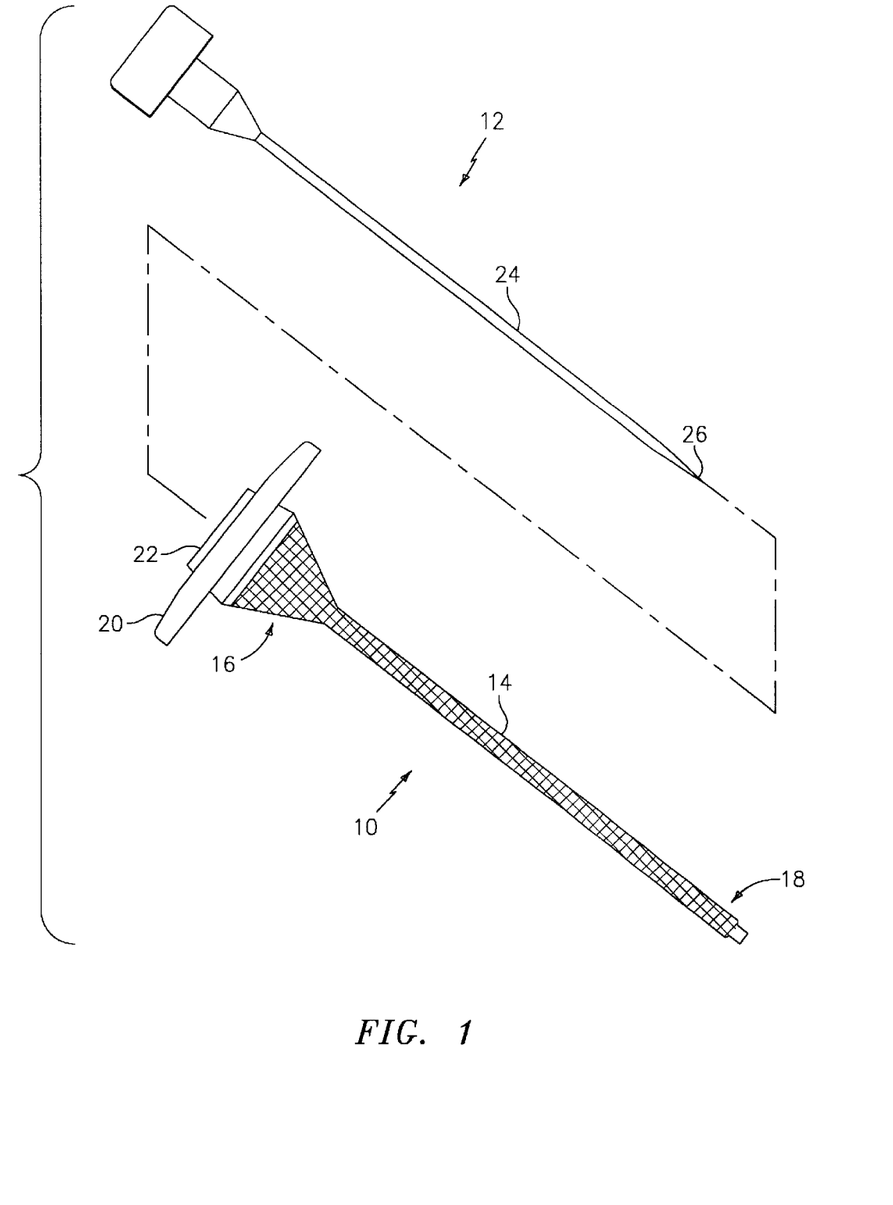
FIG. 1 illustrates a radially expandable sleeve and a needle having a sharpened distal tip which may be received in a lumen of the sleeve to be used in the methods of the present invention.

Referring to FIG. 1, a radially expandable sleeve 10 and needle 12 which may be used in the methods and systems of the present invention are illustrated. The sleeve 10 comprises a tubular sheath 14 having a proximal end 16 and a distal end 18. The proximal end 16 is tapered radially outward in the proximal direction and secured to a handle 20. An aperture (not shown) in the handle is aligned with the expanded diameter of the proximal end 16 and includes a bayonet fitting 22 aligned with the aperture. The tubular sheath 14 may comprise any material which is capable of receiving the assembly of the cannula and dilator to effect radial expansion of the sheath, as described in more detail hereinafter. In the exemplary embodiment, the sheath comprises an inelastic braid covered by an elastic membrane, as generally described in U.S. Pat. No. 5,431,676, the full disclosure of which is incorporated herein by reference. Suitable expandable sleeves 10 may be obtained commercially from InnerDyne, Inc., Sunnyvale, Calif., as part of the STEP system.

The needle 12 may comprise a simple solid core rod 24 having a sharpened distal tip 26. Alternatively, the needle may be cannulated to confirm placement by aspiration or drop tests and/or to facilitate over-the-wire placement. The diameter of the needle will typically be in the range from 1 mm to 2 mm, and advancement of the needle through tissue will generally not result in coring of the tissue. When the needle 12 is placed in the lumen of sleeve 10, the sharpened tip 26 will extend out of the distal end of the sleeve, typically by distance in the range from 1 mm to 3 mm.

Figure 2:
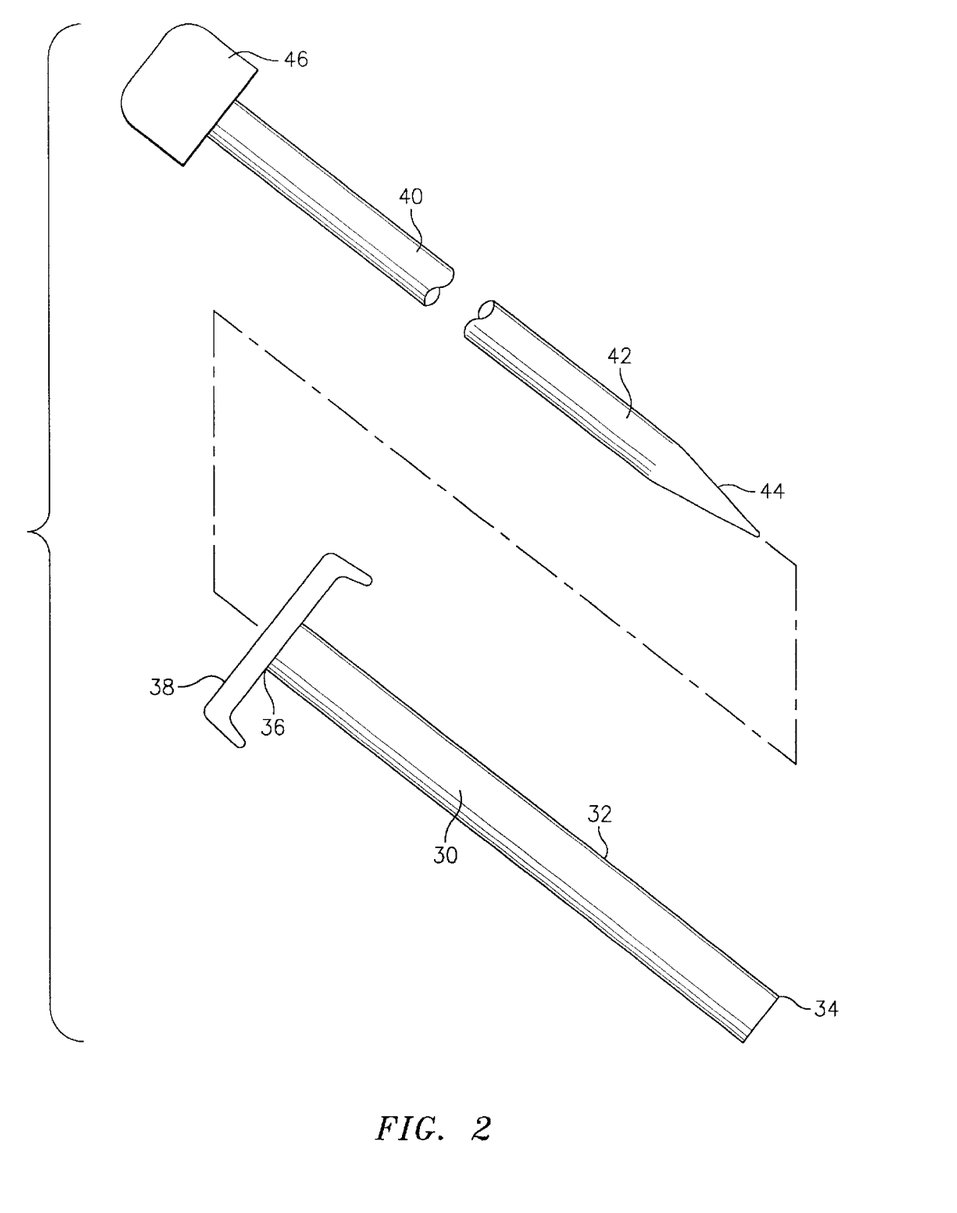
FIG. 2 illustrates a dilator and cannula which may be formed into an assembly and used in the methods of the present invention.

The methods and the systems of the present invention will further utilized an assembly of a cannula 30 and dilator 40, as illustrated in FIG. 2. The cannula 30 comprises a rigid, thin-walled tubular member 32 having a distal end 34 and a proximal end 36. A handle 38 having an aperture aligned with a lumen of the tubular member 32 is attached to the proximal end of the tubular member. The dilator 40 comprises a solid core shaft 42 having a tapered distal end 44 and a handle 46 at its proximal end. The dilator may be removably inserted into the lumen of cannula 30 so that the tapered distal end of the dilator extends distally beyond distal end 34 of the cannula. The lumenal diameter of the cannula will typically be within the ranges set forth above.

Figure 3:
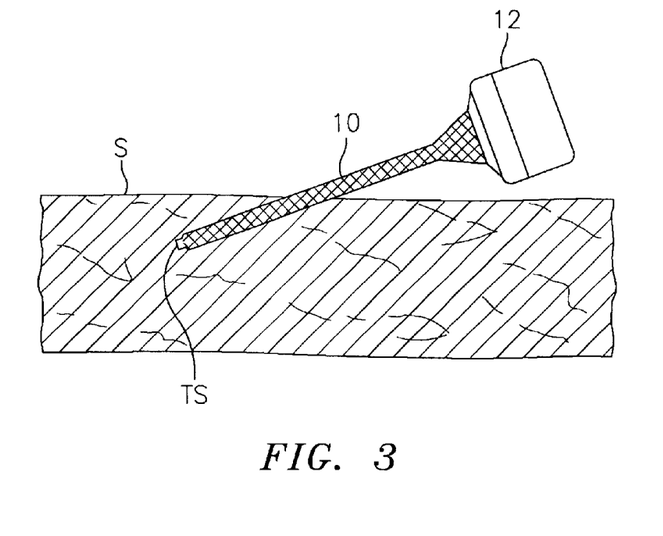
FIGS. 3–10 illustrate the method of the present invention for subcutaneously implanting an article.
Figure 4:
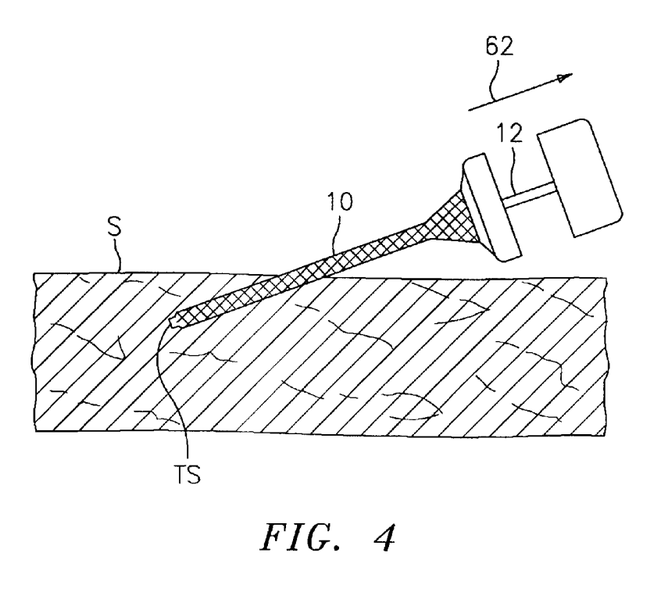
Figure 5:
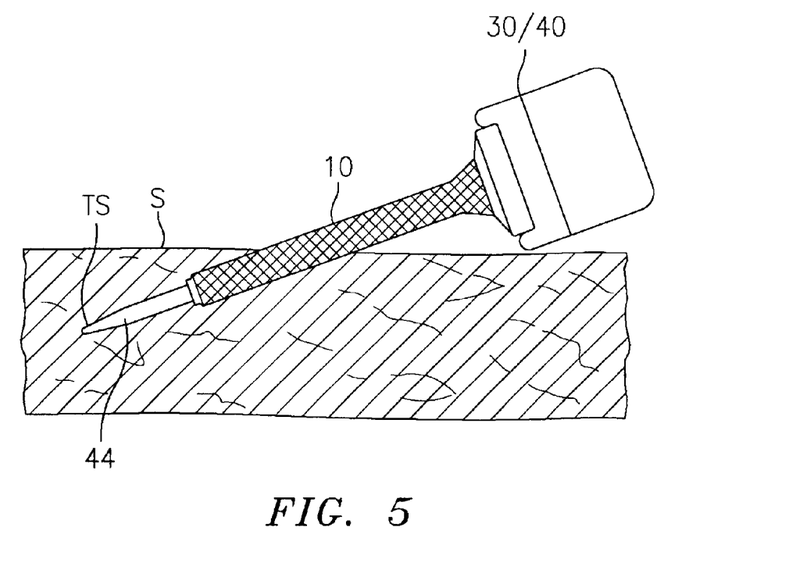
Figure 6:
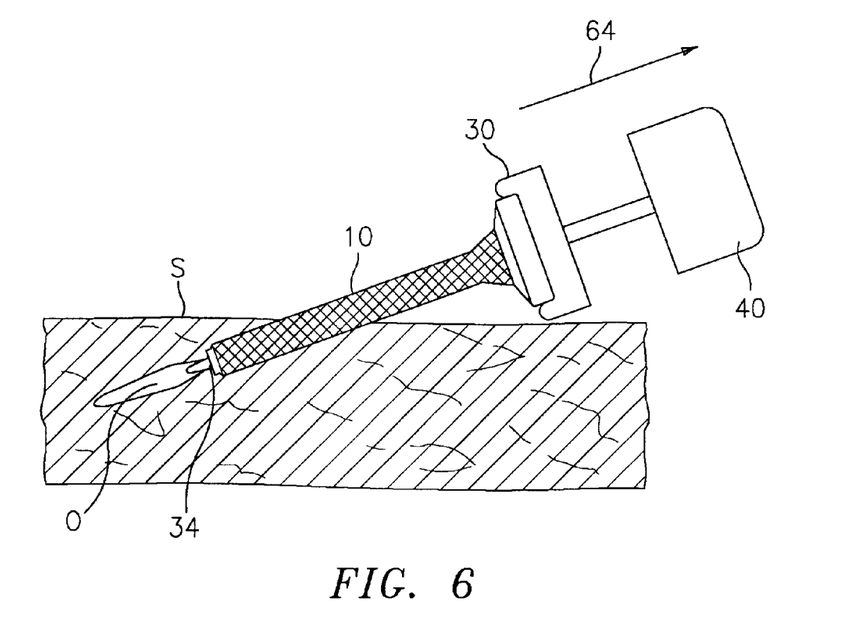
Figure 7:
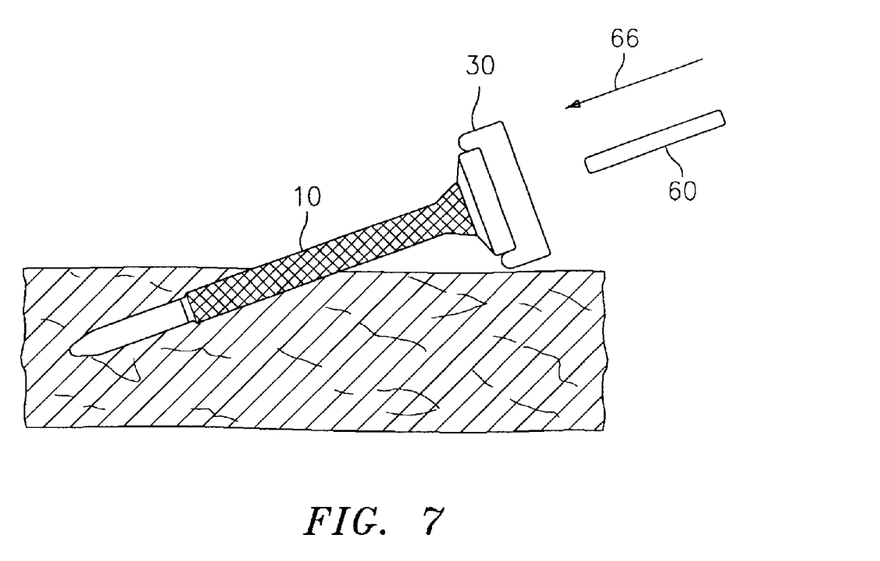
Figure 8:
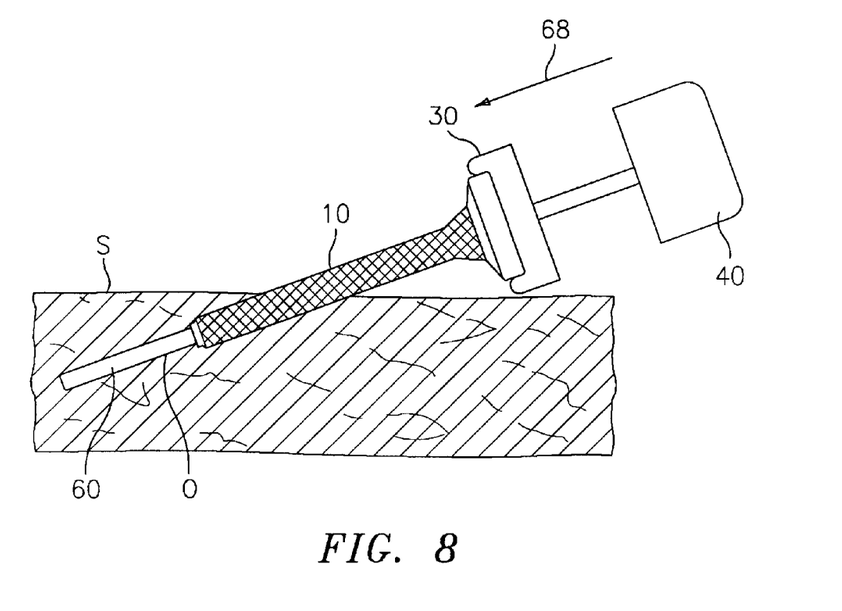

Referring now to FIGS. 3–10, a method according to the present invention for delivering a drug insert 60 (FIG. 7) will be described. Initially, the assembly of sleeve 10 and needle 12 will be percutaneously introduced to a target site TS beneath the patient's skin S (FIG. 3). After reaching the target site TS, the needle 12 is withdrawn in the proximal direction, as shown by arrow 62 in FIG. 4. After fully withdrawing the needle 12, the assembly of cannula 30 and dilator 40 may be introduced through the inner lumen of the expandable sleeve 10, as shown in FIG. 5. The tapered end 44 of the dilator 40 will extend into the tissue at the target site TS. The dilator 40 may then be withdrawn in the proximal direction, indicated by arrow 64 in FIG. 6, leaving the cannula 30 in place within the radially expanded sleeve 10. An opening or potential space O is thus created at the distal end 34 of the cannula 30 after the dilator 40 is withdrawn. The length of the opening will depend on the distance by which the dilator 40 has advanced into the tissue, typically being from 1 mm to 30 mm, usually from 5 mm to 15 mm, depending on the size of the article to be delivered. Alternatively, the opening O could be formed by partially withdrawing the distal end of the cannula 30 prior to insertion of the article to be implanted. The drug insert 60 or other article may then be introduced distally through the lumen of the cannula 30 in the direction of arrow 66, as shown in FIG. 7. Conveniently, the dilator 40 may be used to push the insert 60 so that it extends into the potential space O, as also shown in FIG. 8.

Figure 9:
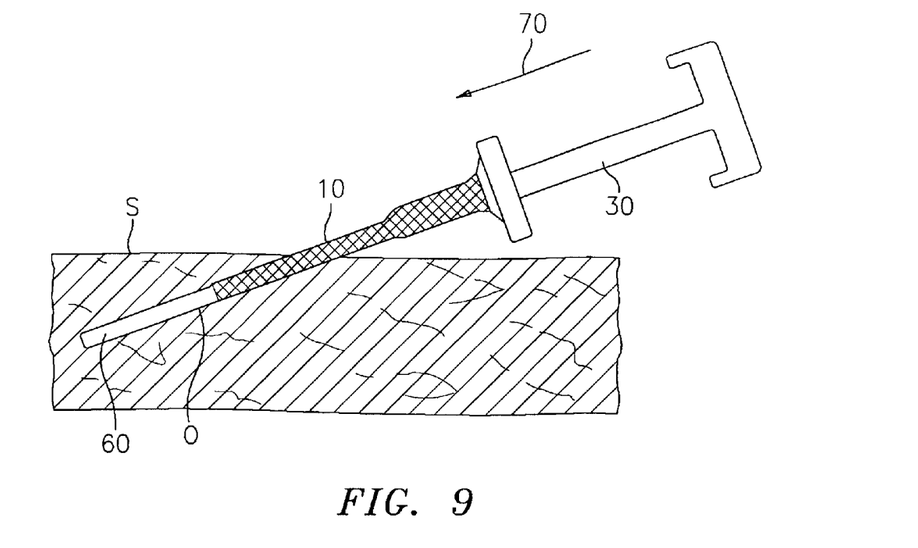
Figure 10:
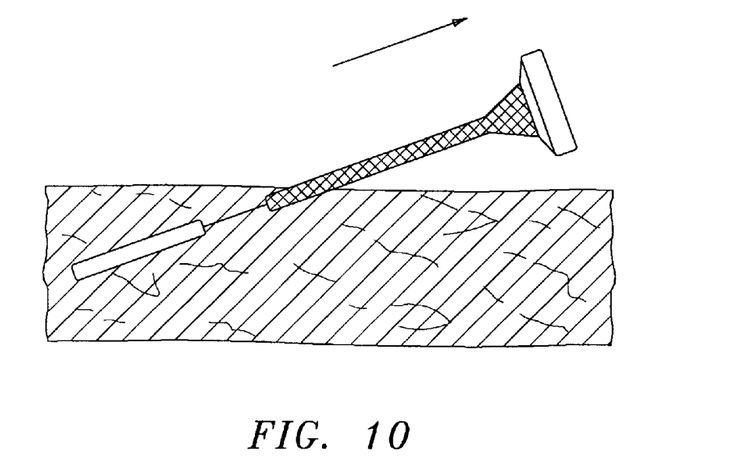

After the insert 60 is fully implanted, as shown in FIG. 8, the dilator 40 may be withdrawn, followed by withdrawal of the cannula 30 in the direction of arrow 70, as shown in FIG. 9. As the cannula 30 is proximally withdrawn, the sleeve 10 will collapse, allowing the sleeve 10 to be readily withdrawn in the direction of arrow 72, as shown in FIG. 10. Collapse of the sleeve lessens trauma to the patient.

Figure 11:
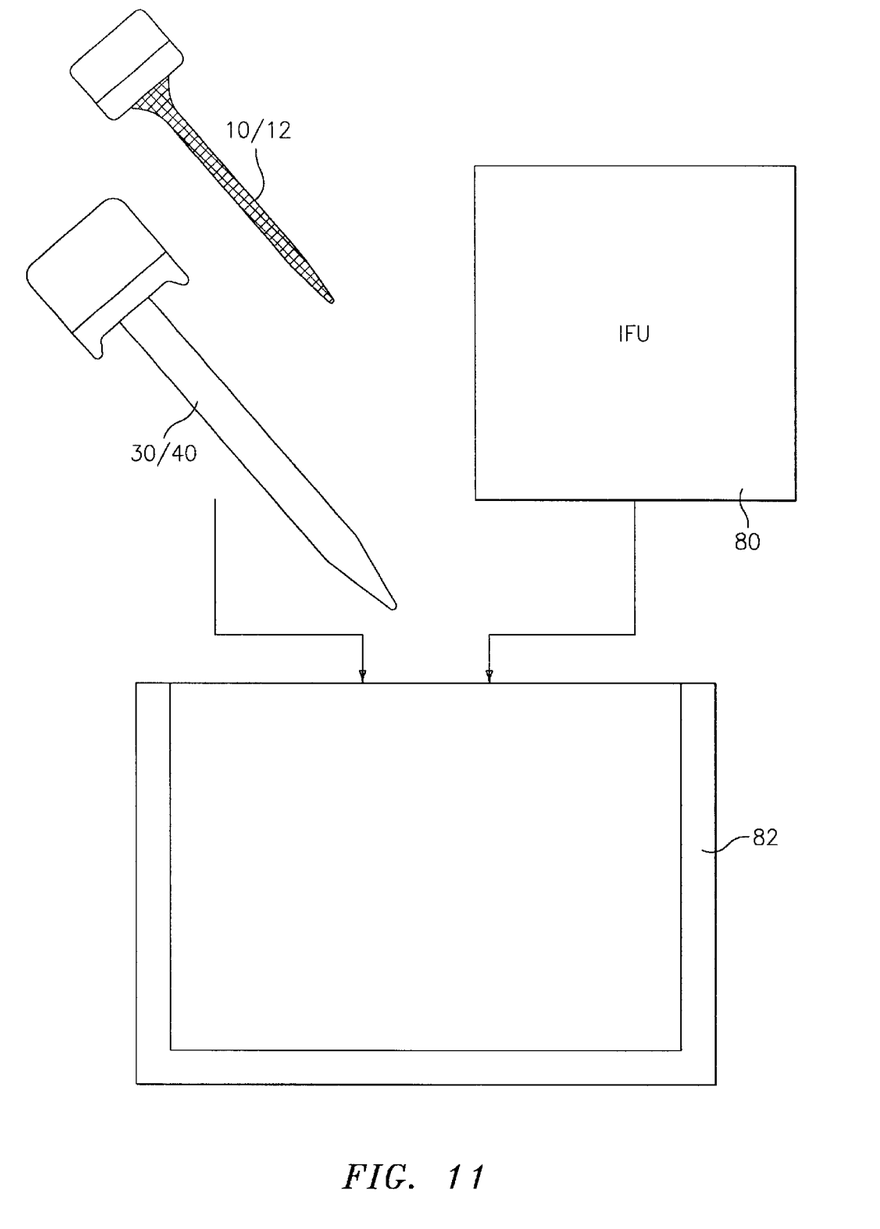
FIG. 11 illustrates a kit constructed in accordance with the principles of the present invention.

Kits according to the present invention will comprise at least some of the components thereof packaged together with instructions for use 80, as shown in FIG. 11. For example, the assembly of radially expandable sleeve 10 and needle 12 may be packaged together with the assembly of cannula 30 and dilator 40 in a pouch 82, or other conventional container, such as tray, tube, box, or the like. The instructions for use 80 will set forth any of the methods described above for percutaneously introducing an article beneath a patient's skin for subcutaneous implantation.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for implanting controlled release medicament delivery articles into solid tissue, said method comprising:
    percutaneously inserting a radially expandable sleeve so that a distal end thereof lies adjacent to a target site in solid tissue;
    introducing an assembly of a cannula and a dilator through the radially expandable sleeve, wherein the diameter of the sleeve is expanded;
    removing the dilator from the cannula to leave an open lumen to the tissue target site;
    advancing at least one controlled release medicament delivery article through the cannula lumen and into solid tissue at the target site; and
    removing the cannula and the radially expandable sleeve in order to leave the at least one controlled release medicament delivery article in place in the solid tissue.

2. A method as in claim 1, wherein the sleeve inserting step comprises advancing an assembly of the sleeve and a needle into the tissue, wherein a sharpened distal tip of the needle is disposed distally of the sleeve to advance through the tissue first.

3. A method as in claim 1, wherein the expandable sleeve comprises a tubular braid formed of a mesh of non-elastic filaments which axially shorten as they are expanded.

4. A method as in claim 1, wherein the assembly introducing step comprises penetrating a tapered distal end of the dilator into the tissue disposed distally of the distal end of the sleeve in order to create an opening in the solid tissue to receive the article.

5. A method as in claim 1, wherein the cannula lumen has a diameter in the range from 2 mm to 20 mm.

6. A method as in claim 1, wherein the inserting step comprises introducing the sleeve intramuscularly or subcutaneously.

7. A method as in claim 6, wherein the article is an implant which releases a drug selected from the group consisting of estrogen, progesterone, and testosterone.

8. An improved method for implanting controlled release medicament delivery articles into solid tissue, said method being of the type wherein a tissue tract is formed and dilated to permit advancement of the article, wherein the improvement comprises:
    radially expanding the tissue tract to form a lumen having a substantially constant diameter by:
        percutaneously inserting a radially expandable sleeve so that a distal end thereof lies adjacent to a target site in solid tissue;
        introducing an assembly of a cannula and dilator through the radially expandable sleeve, wherein the sleeve is radially expandable; and
        removing the dilator from the cannula to leave the substantially constant diameter lumen to the target site;
    advancing at least one controlled release medicament delivery article through the lumen after the lumen has been substantially completely expanded; and
    releasing the at least one controlled release medicament delivery article from the radially expanded lumen into solid tissue at a target tissue site.

9. A method as in claim 8, wherein the sleeve inserting step comprises advancing an assembly of the sleeve and a needle into the tissue, wherein a sharpened distal tip of the needle is disposed distally of the sleeve to advance through the tissue first.

10. A method as in claim 8, wherein the expanded sleeve comprises a tubular braid formed of a mesh of non-elastic filaments which axially shorten as they are expanded.

11. A method as in claim 8, wherein the assembly introducing step comprises penetrating a tapered distal end of the dilator into the tissue disposed distally of the distal end of the sleeve in order to create an opening in the solid tissue to receive the article.

12. A method as in claim 8, wherein the cannula lumen has a diameter in the range from 2 mm to 20 mm.

13. A method as in claim 8, wherein the inserting step comprises introducing the sleeve intramuscularly or subcutaneously.

14. A method as in claim 13, wherein the article is an implant which releases a drug selected from the group consisting of estrogen, progesterone, and testosterone.

15. A system for implanting controlled release drug delivery articles into a patient, said system comprising:
    a radially expandable sleeve, said sleeve being expandable from a narrow diameter configuration to a larger diameter configuration and providing a non-collapsible lumen; and
    at least one controlled release drug delivery article having peripheral dimensions which permit it to be delivered through the non-collapsible lumen, wherein the lumen can remain fully open to its large diameter configuration in the absence of the article therein.

16. A system as in claim 15, further comprising an assembly of a cannula and a dilator removably received in a lumen of the cannula, wherein the assembly is configured to be advanced through the sleeve to radially expand the sleeve and wherein the dilator can be removed from the cannula to leave the non-collapsible lumen through the sleeve.

* * * * *